United States Patent [19]
Kaufman

[11] 4,253,721
[45] Mar. 3, 1981

[54] CABLE CONNECTOR

[76] Inventor: John G. Kaufman, 858 Condor Dr., Burlington, Ontario, Canada, L7T 3A7

[21] Appl. No.: 77,953

[22] Filed: Sep. 24, 1979

[51] Int. Cl.³ .......................................... H01R 13/639
[52] U.S. Cl. ............................................... 339/91 R
[58] Field of Search ........................... 339/75 R, 91 R; 128/798

[56] References Cited

U.S. PATENT DOCUMENTS

| 4,012,098 | 3/1977 | Tolnar, Jr. | 339/91 R |
| 4,061,408 | 12/1977 | Bast et al. | 339/75 R |
| 4,085,991 | 4/1978 | Marshall et al. | 339/91 R |
| 4,094,571 | 6/1978 | Benjamin | 339/91 R |
| 4,200,350 | 4/1980 | Zimmerman, Jr. | 339/91 R |

Primary Examiner—John McQuade

[57] ABSTRACT

A cable connector particularly adapted for attachment to the end of a cable and releasable attachment to a stud fastener such as commonly provided on an electrosurgical electrode, comprises a body portion having a groove therein along which the head of the stud fastener can slide to a contact location defined by a blind end of the slot. Resilient metal contacts are provided within the body of the connector, to form a resilient electrical contact with the head of the terminal at such location. A hinged locking lever is provided, which hinges into a locking position, in which a protruberance extending downwardly from the locking lever engages behind the head of the stud terminal and prevents its withdrawal from the contact location along the slot. The dimensions of the slot prevent withdrawal of terminal in any other direction. The locking lever also has an engaging proturberance which releasably engages a formation on the end of the body, to hold the locking lever in its locked position. The body is made of ultrasound weldable plastic material, from three assemblable plastic parts, each of which individually is a simple plastic molding.

7 Claims, 4 Drawing Figures

CABLE CONNECTOR

FIELD OF THE INVENTION

This invention relates to cable connectors, and more specifically to a means for securing a cable to a protruding stud terminal, in a manner guarding against accidental disconnection of the cable therefrom.

BACKGROUND OF THE INVENTION

In the medical field of electrosurgery and electrical monitoring of body functions, it is necessary to provide a return electrode, attached to the patient's body and providing a return path by means of which electrical current returns from the patient. Such a return electrode, commonly consists of a pad adhered, strapped or otherwise affixed to the patient's body. It has an electrical terminal protruding outwardly from the pad, away from the patient's body, to which the cable is to be attached in electrically conducting manner. Whilst the cable should be removable from the electrode when required, since the electrode is normally a disposable item, it is important that accidental disconnection be avoided, particularly during an electrosurgical operation.

It is common and convenient to provide stud terminals on such body electrodes. By a stud terminal as referred to herein is meant an electrically conductive terminal having a short shank and an enlarged, generally cylindrical head on the shank remote from the electrode. Such stud terminals are electrically connected to the electrode, but are integral, generally rigid formations protruding from the pad to a short extent.

Previous attempts to provide cable connectors for this purpose have suffered from one or more disadvantages. Many of them have been susceptible to accidental disconnection, e.g. by a person interfering with the cable to which it is connected. Others have included a combined locking means and electrical connector to lock the connector rigidly to the stud fastener, but these have tended to be subject to wear on repeated use, with consequent deterioration of the quality of the electrical contact formed. Still others have been satisfactory for use only with one given size of stud fastener, and have allowed no latitude for size discrepancies of the head of the fastener.

It is an object of the present invention to provide a new and improved cable connector for use with stud fasteners.

BRIEF SUMMARY OF THE INVENTION

The present invention provides a cable connector of the aforementioned type which includes a movable locking lever which can be put in a locking position to retain the head of a stud terminal in the desired location, in electrical contact with cable terminals on the connector. The locking lever and its movement, however, are independent of the terminals in the connector, so that the movement of the locking lever does not have any adverse effect on the quality of electrical contact achieved, even after extended numbers of usages. It does not cause any wear of the electrical parts. The locking lever can be positively engaged in its locking position, to maintain the head of the stud terminal in proper location, and only released by deliberate, intentional effort to do so. At the same time, the cable connector is simple and economical to manufacture and use, being made of an insulating plastic material.

Thus according to the present invention there is provided a cable connector for releasably connecting a cable to a protruding stud terminal, said connector having:

a generally flat body;

a terminal head-receiving slot having an open end to permit entry of the stud terminal head in the longitudinal direction of the slot, and a closed end defining a terminal head locating portion of said slot;

the width of said slot, at least in the terminal head locating portion thereof, being arranged to prevent withdrawal of the terminal therefrom in a direction other than longitudinally of the slot;

electrical contact means within the body of the cable connector and positioned to make electrical contact with a terminal head disposed in the terminal head locating portion of said slot;

a locking lever movable relative to the body between the locking position and an unlocking position;

a terminal locking formation extending downwardly from said locking lever and protruding into said slot, when the lever is in its locking position, to prevent removal of a terminal head from the terminal head location in the longitudinal direction of the slot, and to maintain said terminal head in electrical contact with said electrical contact means;

the locking formation being removed from the slot when the locking lever is in its unlocking position.

BRIEF INTRODUCTION TO THE DRAWINGS

In the drawings like reference numerals indicate like parts.

DESCRIPTION OF THE PREFERRED EMBODIMENTS

Figure 1:
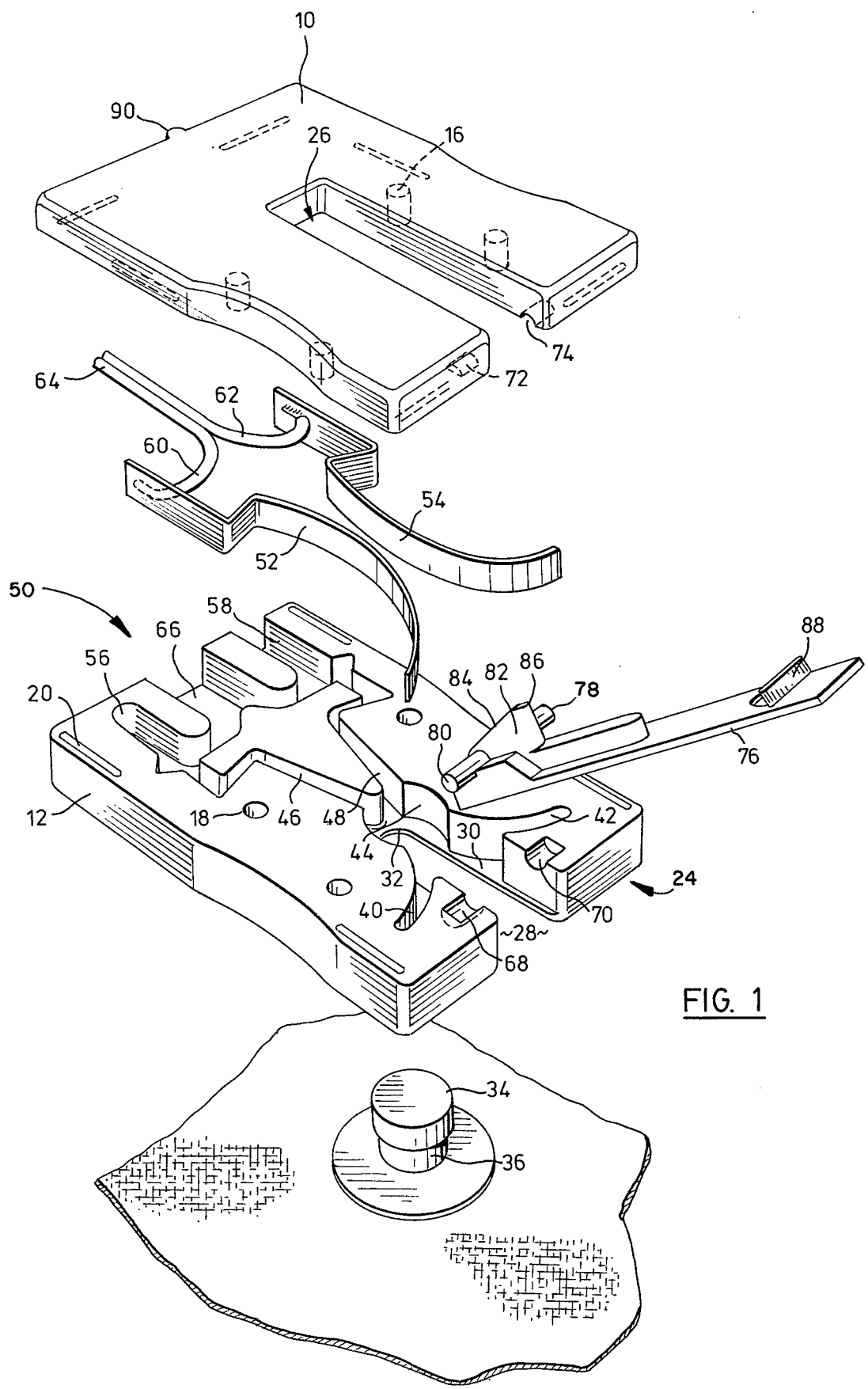
FIG. 1 is an exploded perspective view of a specific preferred embodiment of cable connector according to the invention, with associated stud terminal to which it is releasably attached.

In the preferred form of connector according to the invention, the locking lever is hingedly connected to the body of the connector at a first end of the body adjacent to the open end of the slot, and lies along the length of the slot when in its locking position. Conveniently, for at least a portion of its length, the lever fits into the slot, to make a neater arrangement less susceptible to accidental release of the lever. However, to guard against such accidental release, the preferred embodiment of the invention has a locking lever with a length exceeding that of the body, so that, in its closed locking position, the lever protrudes beyond the second end of the body and has an engaging protruberance extending downwardly therefrom and adapted to engage the body of the connector when in the locking position. A complementary engaging formation may be provided on the end of the connector body, at said second end, to engage against the protruberance on the lever and hold it in the locking position.

The electrical contacts which are provided within the body of the connector of the preferred embodiment are preferably spring metal connectors, which protrude inwardly into the slot at the terminal head locating area. Then, when the terminal head is introduced, the electrical spring connectors are resiliently spring urged into contact with the terminal head, to give good electrical contact.

Thus, the operation of the locking lever, to lock and release the terminal head from its electrically contacting location, is quite independent of the terminal means located in the connector. Repeated use of the terminal connector, by repeated operation of the locking lever, does not have any effect on the efficiency of electrical connection provided by the spring loaded electrical contacts. Moreover, the arrangement of locking lever, with its protuberance for releasably engaging the body to hold it in the locking position, satisfactorily safeguades against any accidental release thereof.

The locking protuberance extending downwardly from the locking lever suitably has a lower incline bottom surface sloping downwardly in the direction away from the hinged connection, and a shoulder presented towards the closed end of the slot at the terminal of the inclined bottom surface. Then, when the terminal is introduced along the slot, it pushes the lever upwards as it proceeds, by engagement with the sloping bottom surface thereof. When it passes the inclined surface, and falls behind the shoulder for engagement in the correct position, a visual signal is given to the operator that the terminal in is the correct position, by the consequent lowering of the lever.

The connector is conveniently manufactured in three separate parts, namely an upper body part, a lower body part and a locking lever, each of which may be of plastic, suitably an ultra sound weldable plastic such as Lexan Polycarbonate, so that the body part can be easily assembled and joined together by ultrasound welding. Each of the three plastic parts can be made in a simple injection molding or plastic stamping operation.

DETAILED DESCRIPTION OF THE SPECIFIC PREFERRED EMBODIMENT

Figure 2:
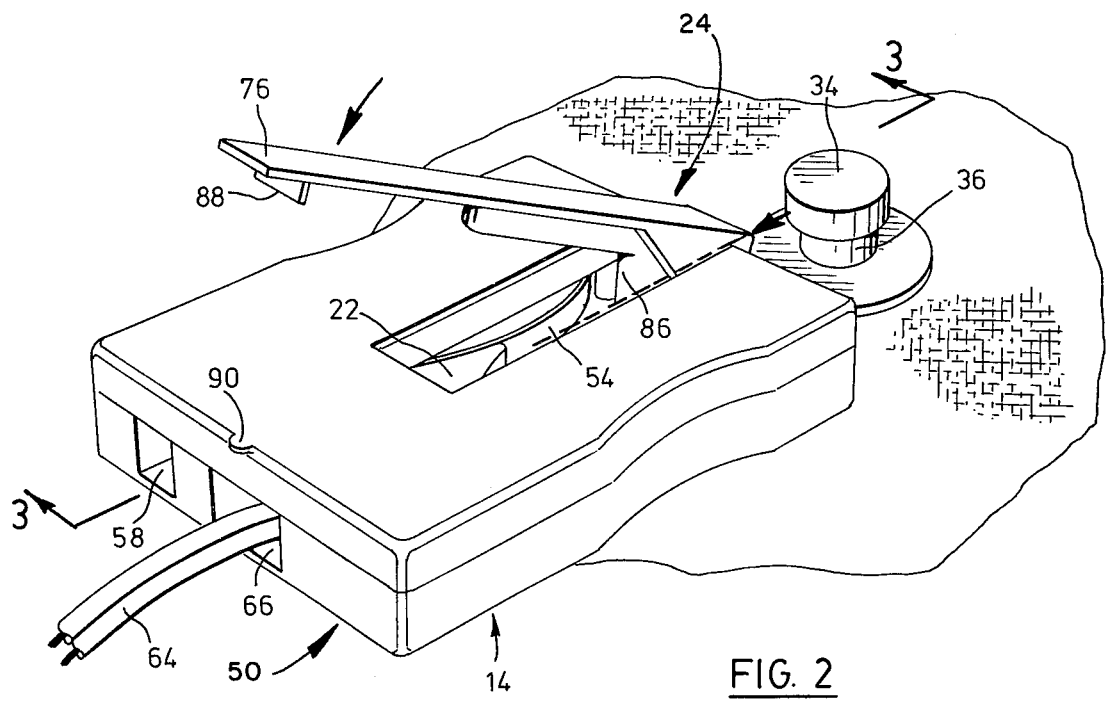
FIG. 2 is a perspective view of the assembled connector of FIG. 1.

Referring now to the drawings, the cable connector according to the specific preferred embodiment has an upper, generally rectangular body part 10 and a slower generally rectangular body part 12, both of ultrasound weldable plastic, and having outer peripheries adapted to coincide and to interfit, to form an assembled generally flat rectangular connector body 14 (FIG. 2). The downwardly presented face of upper body part 10 is provided with protrusions 16 which on assembly fit into respective recesses 18 on the upper surface of lower body part 12, for correct location of the parts on assembly. Also, both said mating surfaces are provided with small "reservoirs" of plastic, in the form of ridges 20, which are melted and used on welding the parts together with ultrasound.

The assembled body 14 of the connector is provided with a longitudinally extending slot 22, extending from and open at the first end 24 of the body 14 to the approximate middle of the length of the body 14. The slot 22 is formed by two similar slot formations 26, 28, respectively, provided in the upper and lower body parts 10, 12. The slot formation 26 in the upper body part 10 is slightly longer than that in the lower body part 12. The lower slot formation 28 is provided with a side shelf 30 which defines the narrowest width of slot 22 when the body is assembled, and forms a semicircular closed end 32 of slot 22. The head 34 of a stud terminal 36 can enter slot 22 and move to the centre of the body 14 until it engages closed end 32. The side shelf 30 engages against the underside of terminal head 34 to prevent its removal downwardly from slot 22. The closed end 32 of the slot provides a terminal head locating portion of the slot 22.

The main thickness of lower body part 12, above the level of shelf 30, is provided with a pair of curved channels 40, 42 extending towards the first end 24 of the body, on either side of slot formation 28, a part circular recess 44 surrounding closed end 32, and a pair of generally S-shaped channels 46, 48 extending from recess 44 towards the second end 50 of the body. In the assembled unit, these receive respective spring metal electrical contacts 52, 54 so that the contacts lie either side of slot 22 in the terminal head locating portion and protrude resiliently into the slot 22 to make good electrical contact with terminal head 34 when it is disposed therein.

The ends of channels 46, 48 nearest to the second end 50 of the body communicate with respective enlarged recesses 56, 58 where the ends of metal contacts are soldered to wires 60, 62 of the cable 64. Both recesses 56, 58 communicate with an end recess 66 at the second end 50 of the body, through which cable 64 leaves the assembled body. Enlarged recess 58 also communicates through second end 50 of the assembled body 14 to allow passage of the second cable into the interior of the body 14 in alternative uses of the cable connector.

Near its first end 24, the lower body part 12 is provided on its upper surface with a pair of aligned, transversely extending semicircular depressions 68, 70, one on either side of its slot formation 28. Similar complimentary depressions 72, 74 are provided in the lower surface of upper body part 10 to form generally circular bearing recesses in the assembled body. A locking lever 76 is provided, having a pair of integral cylindrical protrusions 78, 80 extending laterally near its one end, and received in these generally circular bearing recesses so as hingedly to connect the lever 76 to the assembled body 14 near its first end 24, adjacent to the open end of slot 22.

Figure 3:
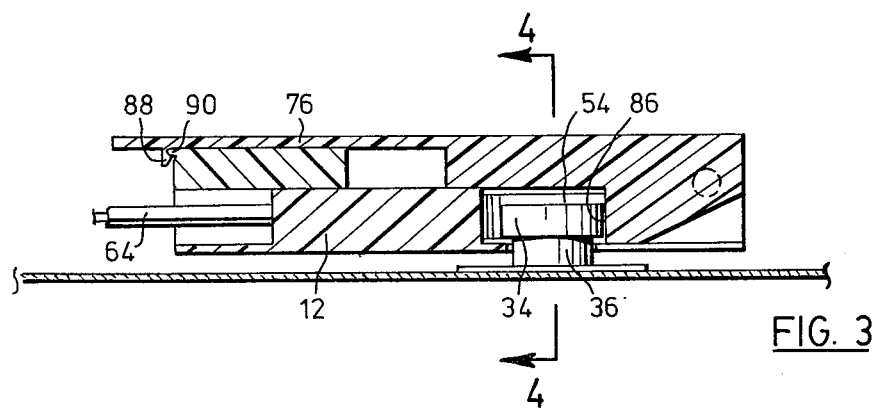
FIG. 3 is a sectional view along the line 3—3 of FIG. 2.
Figure 4:
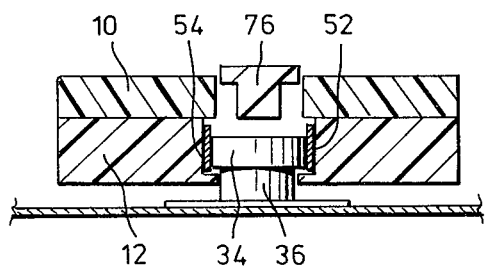
FIG. 4 is a sectional view along the line 4—4 of FIG. 3.

The locking lever 76 has an integral terminal locking formation 82 protruding downwardly therefrom near its first end, the body formation 82 having a lower inclined bottom surface 84 sloping downwardly in a direction away from its hinged connection, and a shoulder 86 presented towards the closed end of the slot 22. As shown in FIG. 3, the locking lever 76 has a length to extend beyond the second end 50 of the body 14, and has an engaging protruberance 88 near its end which extends downwardly from the lowered lever 76. A complimentary engaging formation 90 is provided on the second end 50 of the body 14, which will engage protruberance 88 to hold the lever 76 in its locked position along slot 22.

The assembly and operation of the device will be apparent from the foregoing description. The parts are assembled as shown in FIG. 1, and then the two body parts 10, 12 are ultrasound welded together to give the unitary item 14 shown in FIG. 2. With the locking lever 76 raised in its unlocking position, as shown in FIG. 2, the stud terminal head 34 can enter slot 22 and be moved along it until it engages against the end 32 of the slot. As it does so, it bears against the inclined bottom surface 84 of locking protuberance 82 on the lever 76, and raises the lever until it passes beyond shoulder 86, whereupon the lever will fall again. Thus the operator has a clear signal that the head 34 of stud terminal 36 has achieved its correct, connecting position. It is then disposed in the terminal head locating portion of the slot, where it engages spring metal electrical contacts 52, 54, which are resiliently urged against it to form good electrical contact. Now the locking lever 76 is lowered, into its locking position on the body 14 as shown in FIG. 3, with its protruberance 88 engaging body formation 90 to hold it in the locked position. The shoulder 86 of locking protruberance 82 prevents withdrawal and electrical disconnection of terminal 36 along the slot whilst locking lever 76 is in its locking position. Shelf 30 prevents other withdrawal of the terminal. Thus the parts remain securely fastened together, to resist any accidental pulls on cable 64 or terminal 36.

To disconnect the parts requires a deliberate, but simple, disengagement of protruberance 88 and formation 90 and subsequent lifting of the locking lever 76 to its unlocked position shown in FIG. 2. Then the terminal can be simply withdrawn along slot 22.

Whilst a specific preferred embodiment of the invention has been illustrated and described in detail herein, it will be appreciated that this is for purposes of illustration only, and not by way of limitation. The scope of the invention is limited only by the scope of the appended claims.

I claim:

1. A cable connector for releasably connecting a cable to a protruding stud terminal, said connector having:

a generally flat body;

a terminal head-receiving slot in the flat body having an open end to permit entry of the stud terminal head in the longitudinal direction of the slot, and a closed end defining a terminal head locating portion of said slot;

the width of said slot at least in the terminal head locating portion thereof, being arranged to prevent withdrawal of the terminal therefrom in a direction other than longitudinally of the slot;

electrical contact means within the body of the cable connector and positioned to make electrical contact with the terminal head disposed in the terminal head locating portion of said slot;

a locking lever movable relative to the body between a locking position and an unlocking position;

a terminal locking formation extending downwardly from said locking lever and protruding into said slot, when the lever is in its locking position, to prevent removal of a terminal head from the terminal head locating portion in the longitudinal direction of the slot and to maintain said terminal head in electrical contact with said electrical contact means;

the locking formation being removed from the slot when the locking lever is in its unlocking position.

2. The cable connector of claim 1 wherein said locking lever is hingedly connected to the body of the connector, at a first end of the body adjacent to the open end of said slot, and lies along the length of the slot when in its locking position.

3. The cable connector of claim 2 wherein the locking lever has a length exceeding that of the body so as to protrude beyond the second end of the body when in its locking position, said lever having an engaging protruberance extending downwardly therefrom and adapted to engage the body of the connector when in the locking position, so as to hold the locking lever in its engaged position.

4. The cable connector of claim 3 wherein the engaging protruberance of said locking lever is located adjacent its end remote from its hinged connection, and the body is provided with a complementary engaging formation on the edge of its second end, to engage the engaging protruberance on the locking lever when the locking lever is in its locking position.

5. The cable connector of claim 4 wherein the electrical contact means comprises a pair of spring metal contacts, one on each side of the terminal head locating portion of said slot, and resiliently protruding into said slot.

6. The cable connector of claim 5 wherein the electrical contact means are electrically connected to a cable within the body of the connector, said cable protruding from the second end of said body.

7. The cable connector of claim 3 wherein the locking protruberance extending downwardly from said locking lever comprises a lower inclined bottom surface sloping downwardly in the direction away from the hinge connection, and a shoulder presented towards the closed end of the slot, at the termination of said inclined bottom surface.

* * * * *